(12) United States Patent
Mattchen

(10) Patent No.: US 7,207,090 B2
(45) Date of Patent: Apr. 24, 2007

(54) HIGH TENSION, SURGICAL CABLE LOCK

(75) Inventor: Terry M. Mattchen, Santa Barbara, CA (US)

(73) Assignee: Kinamed, Inc., Camarillo, CA (US)

( * ) Notice: Subject to any disclaimer, the term of this patent is extended or adjusted under 35 U.S.C. 154(b) by 0 days.

(21) Appl. No.: 11/147,685

(22) Filed: Jun. 8, 2005

(65) Prior Publication Data

US 2005/0273983 A1 Dec. 15, 2005

Related U.S. Application Data

(60) Provisional application No. 60/578,611, filed on Jun. 9, 2004.

(51) Int. Cl.
*F16G 11/00* (2006.01)
(52) U.S. Cl. ............... 24/136 R; 24/115 R; 24/136 K; 439/783
(58) Field of Classification Search ............ 24/136 R, 24/115, 136 K, 136 L, 136 B; 439/783, 439/115 M
See application file for complete search history.

(56) References Cited

U.S. PATENT DOCUMENTS

| | | | | | |
|---|---|---|---|---|---|
| 3,953,144 | A | * | 4/1976 | Boden | 403/374.2 |
| 4,059,333 | A | * | 11/1977 | Mixon, Jr. | 439/783 |
| 5,244,422 | A | * | 9/1993 | Laricchia | 439/783 |
| 6,842,949 | B2 | * | 1/2005 | Warren | 24/135 N |

* cited by examiner

*Primary Examiner*—Robert J. Sandy
*Assistant Examiner*—Marcus Menezes
(74) *Attorney, Agent, or Firm*—William L. Johnson

(57) ABSTRACT

A cable retaining device is suitable for retaining flexible cables at high load tensions. The device includes: a body including a void having a width that tapers from a wider rearward end to a narrower forward end; and a wedge shaped plug, capable of slidable insertion at least partially into said void. The wedge and the plug define at least one channel between them, said channel capable of receiving a cable. The channel is tapered from a narrower rearward orifice to a wider forward orifice. The invention also includes a system of the cable retaining device together with a high-tension polymer cable, said system suitable for surgical use. Furthermore, the invention includes the method of fastening cable with the cable retaining device of the invention. In one embodiment the device retains a looped cable by engaging two cable ends.

18 Claims, 4 Drawing Sheets

HIGH TENSION, SURGICAL CABLE LOCK

This application claims priority of provisional application Ser. No. 60/578,611, filed in the U.S. Patent office on Jun. 9, 2004.

BACKGROUND OF THE INVENTION

1. Field of the Invention

This invention relates to devices for locking cords against longitudinal movement generally, and more specifically to devices for retaining surgical cables under high tension, suitable for surgical implantation in a human body.

2. Description of the Related Art

Cable locks based on the principle of the wedge are known. Consider, for example, the lock described in U.S. Pat. No. 4,156,576. Such cable locks employ a wedge as a simple machine for securing cordage.

At high tensions, certain modern polymer based cords seem to defy all attempts to engage and lock the cord, dramatically curtailing their range of practical use. Several of the material properties of polymer fibers tend to complicate efforts to fasten polymer cords. The surfaces tend to be slippery; the materials have memory, which tends to unravel knots; and in some circumstances the materials tend to deform and flow (as implied by the common term "plastic"). For these reasons, conventional knots are inadequate. Other clasps and fasteners tend to lose purchase in the cords, and under high tension the polymer cords tend to slip. Attempts to counteract slippage by application of increased pressure often result in cutting or fraying of the cord.

As disclosed in U.S. Pat. No. 6,589,246, certain polymer cables have shown promise for surgical use. However, their widespread acceptance depends in part on the availability of an efficient, economical, convenient and reliably means of clamping or retaining the cable under moderate to high tension.

SUMMARY OF THE INVENTION

In view of the above problems, the present invention includes a cable retaining device, suitable for retaining flexible cables at high load tensions. The device includes: a body including a void having a width that tapers from a wider rearward end to a narrower forward end; a wedge shaped plug, capable of slidable insertion at least partially into said void. The wedge and the plug define at least one channel between them, said channel capable of receiving a cable. The channel is tapered from a narrower rearward orifice to a wider forward orifice.

The invention also includes a system of the cable retaining device together with a high-tension polymer cable, said system suitable for surgical use. Furthermore, the invention includes the method of fastening cable with the cable retaining device of the invention These and other features and advantages of the invention will be apparent to those skilled in the art from the following detailed description of preferred embodiments, taken together with the accompanying drawings, in which:

DETAILED DESCRIPTION OF THE INVENTION

The applicant has discovered that certain innovative cables are difficult to reliably engage and fix by conventional fasteners. At high tensions, certain modern polymer based cords seemingly defy attempts to engage and lock the cord, dramatically curtailing their range of practical use. Several of the properties of polymer materials tend to complicate efforts to fasten polymer cords. The surfaces tend to be slippery; the materials have memory, which tends to unravel knots; fiber diameters change significantly during stretching; and in some circumstances the materials tend to deform and flow (as implied by the common term "plastic" ). For these reasons, conventional knots are inadequate. Other clasps and fasteners tend to lose purchase in the cords, and under high tension the polymer cords tend to slip. Attempts to counteract slippage by application of increased local pressure often result in cutting or fraying of the cord.

The difficulties of fastening polymer cords have limited their application as surgical cables, causing most surgeons to rely on metal cables, despite the disadvantages of metal cables in a biological setting.

The cable lock of the present invention is adapted to facilitate reliable fixation of high tension, challenging cordage such as surgical cables based on jacketed polymeric materials. For example, the invention is particularly well adapted to engage and hold cables such as those described in U.S. Pat. No. 6,589,246 (Hack and Mattchen, 2003). That patent concerns a surgical use of an engineered polymer cable formed of a polymer core having a plurality of outer fibers that are braided to form a reinforcing jacket. In some embodiments, an outer coating may be applied over the braided fibers. The core is of a polymeric material, such as nylon, polyester, polyethylene or fluorocarbon, that has been processed by several cycles of stretching and tempering using methods commonly applied today. The braided fibers are of a high strength, non-stretch material that are braided over the polymer core.

In one embodiment, the invention includes a combination of a particular cable with the cable lock described herein.

Figure 1:
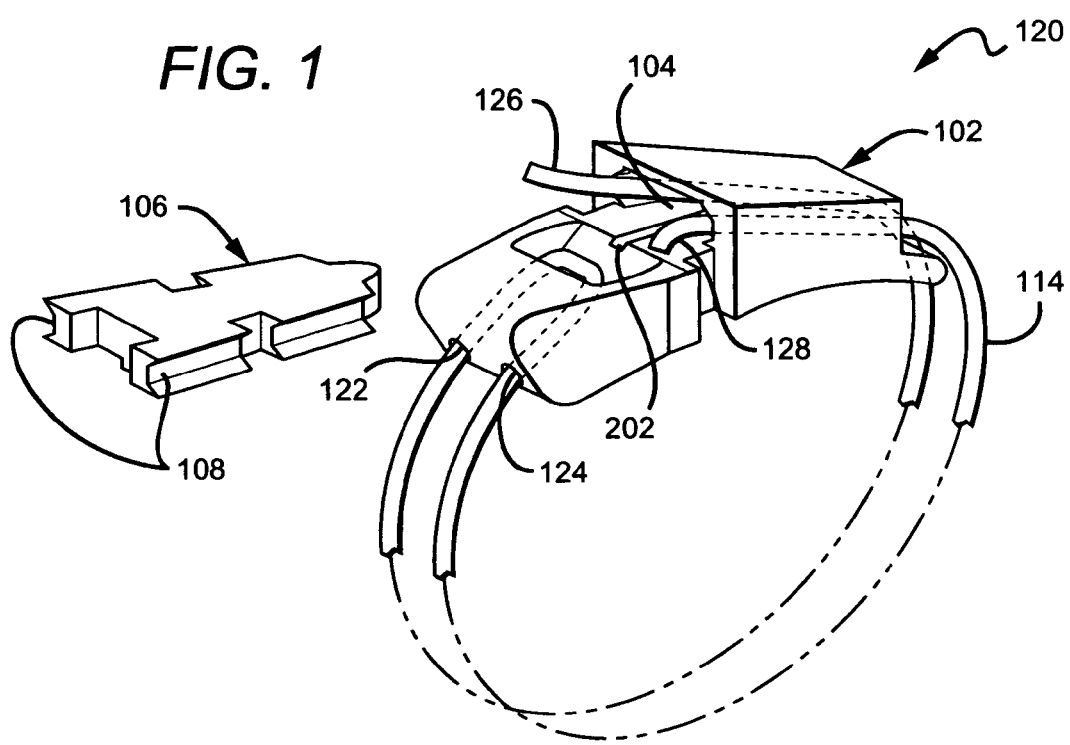
FIG. 1 is a perspective view, partially exploded, of a cable clamp in accordance with the invention.

As Shown (exploded) in FIG. 1, the cable lock of the present invention comprises a body 102 having an internal tapered passage 104, and a relatively moveable, generally wedged shaped plug 106 receivable in the passage 104. As further described below, at least one edge of the plug 106 has a trough or groove 108. When the plug 106 is inserted into said passage 104 of the body 102, the trough 108 in the plug 106 faces a complementary groove or slot in an internal surface of said body 102. The complementary slots (one on the plug, one in the body) together define at least one channel suitable for receiving a surgical cable 114. Preferably, two or more such channels are defined (for example, on opposing sides of the plug 106 as shown in FIG. 1). These features are described with more particularity below, in connection with the various views.

In the preferred embodiment, two troughs 108 are disposed as shown, on opposite sides of the plug 106. The two channels of the preferred embodiment are most suitable for receiving two cables (or both ends of a single cable), which may be retained, fastened, and tensioned by the body and plug assembly (generally denoted 120). More particularly, the body, cables, and plug can be assembled loosely and will thereafter be locked by the tension applied to the cable ends, which will tend to draw the wedged plug into the passage. As the wedged plug is drawn by the tensioned cable into the passage, dual channels will tend to constrict about the cable(s) (due to the generally wedged shape of passage and included plug). Thus, the cable tension tends to sustain the locked engagement of the cable-lock.

In one embodiment the plug has an additional feature adapted to retain a looped cable: for example, the body as shown in FIG. 1 includes two contoured channels 122 and 124 through which the cable 114 can be looped as shown. In one method of using the cord lock, a doubled cord is looped through the plug with the plug disposed near the center of a doubled cable. The two strands of a (doubled) cable are then available, for example to surround a fractured bone or some system to be secured by lashing or "cerclage." The two free ends 126 and 128 are then inserted into the body 102. The cord is then tensioned to a working tension and the plug is inserted into the body with the free cord ends included in the channels defined between the plug and body. Once the plug is firmly planted in the body, the cable tension will retain the plug in the body, securing the system of body, cable and plug in a locked state.

Figure 2:
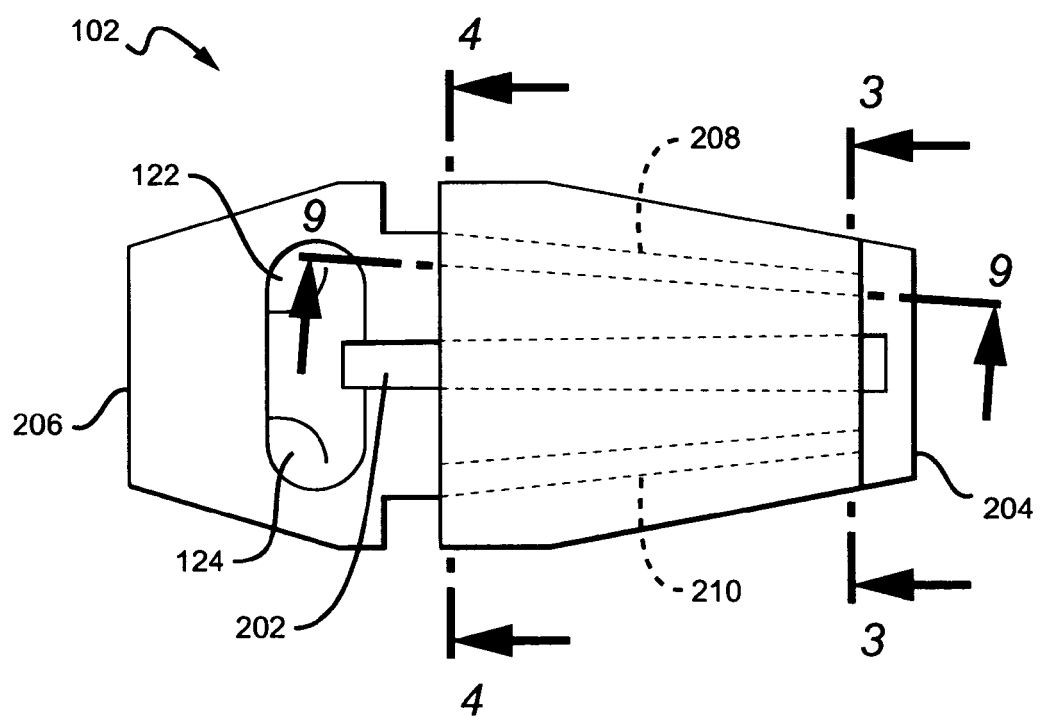
FIG. 2 is a plan view of the cable clamp body.

FIG. 2 shows the body of the cable lock with plug 106 inserted. A guide slot 202 is optionally provided under and generally centered in the passage 104, to facilitate centering the plug for assembly. The body 102 has a generally wider rearward end 206, a generally narrower forward end 204, where it should be understood that "forward" refers to the direction of the loaded or tensioned portion of the cable to be locked. The rearward end 206 thus is defined as oriented toward the free or unloaded end of the cable. These definitions shall be applied throughout this description, unless a contrary usage is explicitly indicated.

The body 102 has a tapered passage 104 adapted to receive the tapered plug 106. The passage 104 has two opposing internal sides (defined by hidden lines 208 and 210 which taper inward from a wider rear to a narrower forward aperture (shown in FIGS. 3 and 4, discussed below). Plug 106 and passage 104 are generally tapered in a complementary manner, so that plug slides easily into the passage until the exterior sides of the plug meet the interior sides of the passage. Forward progress is then resisted because the plug becomes wedged in the passage.

Note that throughout this description, a distinction has been strictly observed between the words "channel" and "passage", which denote distinct features. "Passage" (104) is used to indicate a void or opening in the body 102, capable of receiving the plug 106; "Channel" is used to denote one of the at least one through channels (302 and 304) defined between the body 102 and plug 106, each capable of receiving a cable.

Figure 3:
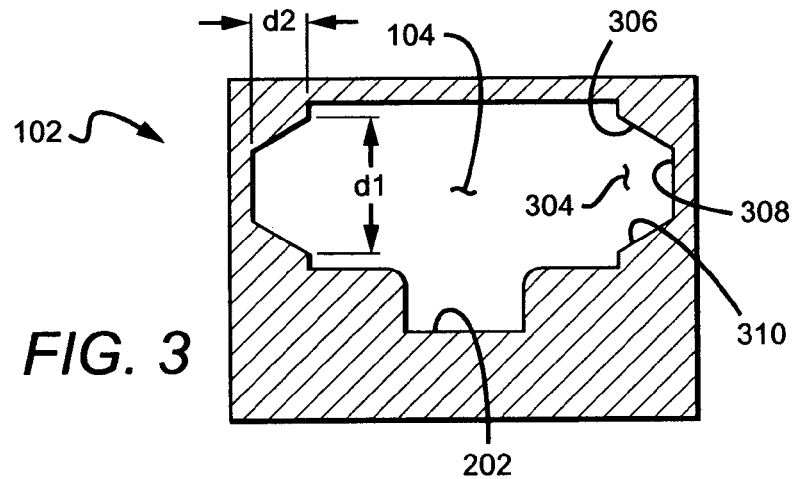
FIG. 3 is a sectional view of the body (plug removed) taken along section line 3 (shown in FIG. 2)

As shown in FIG. 3, At least one and preferably two side walls of the passage 104 are chamfered or beveled, concave inward, having a plurality of elongated plane faces 306, 308 and 310 generally defining a trough or groove with a polygonal cross section. The troughs (defined by 306–310) run generally along the lengths of at least one side 208 or 210 of the passage 104. In one embodiment, both opposing sides of the passage 104 are recessed with three elongated plane surfaces (306, 308 and 310), the surfaces meeting at a dihedral angle of approximately 60 degrees. The cross section of each trough thus resembles a bisected hexagon.

Also as shown in FIG. 3, at the front aperture the two troughs have dimensions denoted d1 and d2 as shown. These dimensions are defined for comparison with the corresponding dimensions at the rear aperture, described below.

Figure 4:
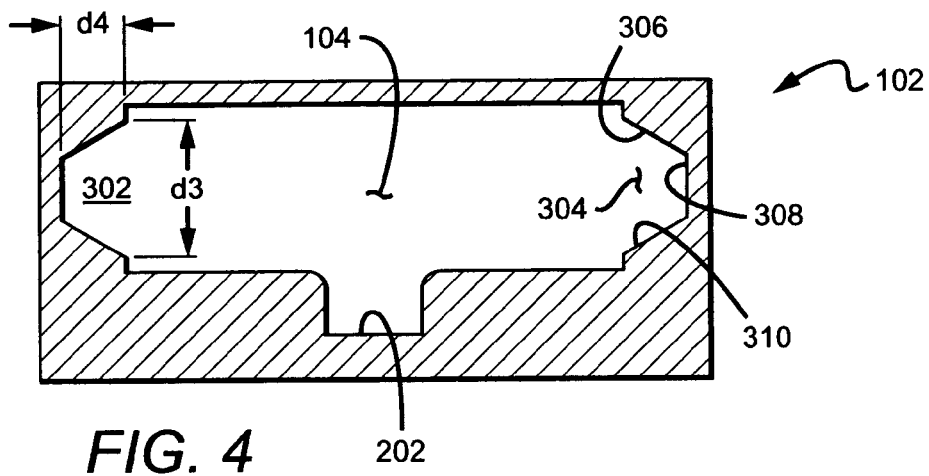
FIG. 4 is another sectional view of the body (plug removed) taken along section 4 in FIG. 2.

The rear aperture is clearly seen in FIG. 4. The overall shape is similar to that of the front aperture, but in the preferred embodiment it is significant that the dimensions d3 and d4 of the recessed side troughs at section line 4 are smaller than the corresponding dimensions (d1 and d2) of the front aperture. The troughs thus flare slightly outward, moving from rear to front aperture. When combined with the complementary plug the effect is to define two cable channels 302 and 304, which flare in a hornlike manner, slightly outward moving from rear to front (in the opposite direction from the taper of the overall passage 104 and plug 106). The flare is suitably linear, due to the generally plane surfaces defining the channel. This unusual forward-flaring channel design has been found unexpectedly advantageous in securing polymer cables at high tension.

Figure 5:
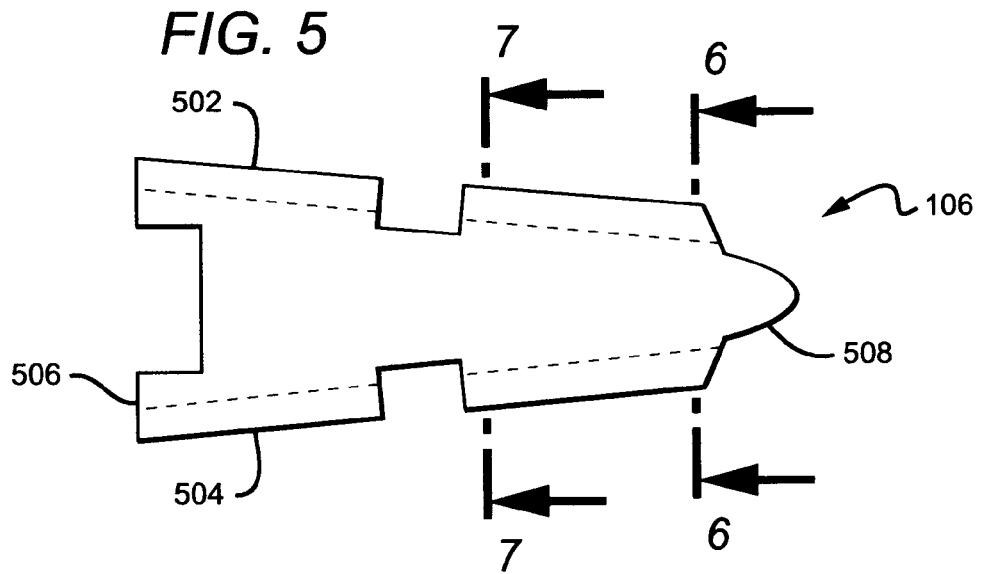
FIG. 5. is a plan view of the plug, removed from the body of the cable clamp.
Figure 6:
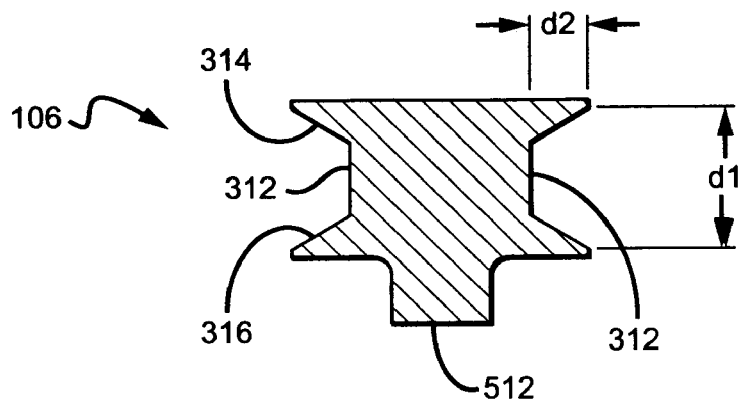
FIG. 6 is a sectional view of the plug, taken along section line 6 in FIG. 5.
Figure 7:
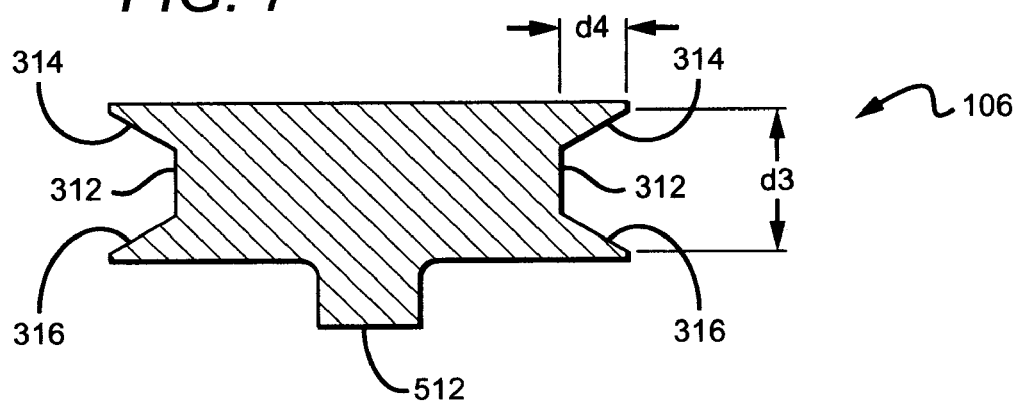
FIG. 7 is another sectional view, taken along section line 7 in FIG. 5.

The plug 106 is shown separately in FIGS. 5, 6 and 7. The plug is generally trapezoidal in plan (FIG. 5), having sides 502 and 504 that taper from a wider rear end 506 to a narrow front end 508. A forward sectional view (FIG. 6) reveals that the sides (at least one) have beveled recessed faces that describe a groove or trough running the length of the plug. Said groove or trough has a plurality of plane faces 312, 314 and 316 meeting at concave dihedral angles, and complementary to those of the body 102 as described above. Rearward section (FIG. 7) is similar in shape. As with the corresponding dimensions of the body, d1 is greater than d3; similarly, d2 is greater than d4, defining forward flaring troughs.

The forward flare of each channel should not be confused with the angle defined between the channels, which is converging moving from the rear to the front of the body. In one embodiment, the channels generally converge toward one another at an angle of approximately 12 degrees.

Figure 8:
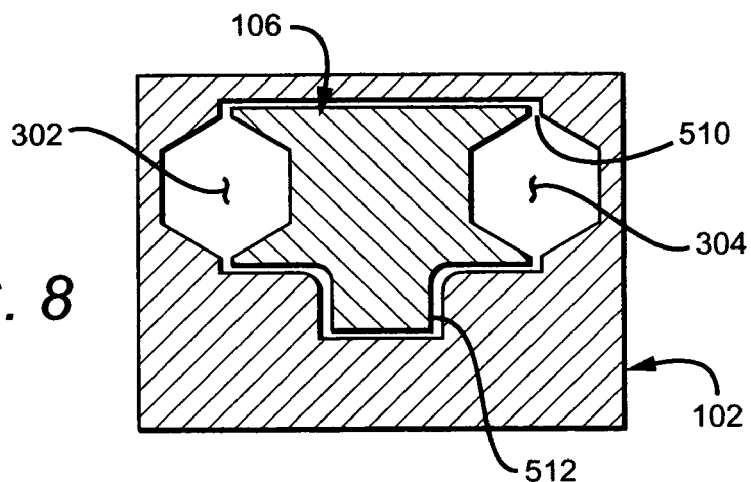
FIG. 8 is another sectional view taken along section line 3 in FIG. 2, showing the section with plug inserted into the body in correct position to retain a cable.

FIG. 8 shows plug 106 inserted into the body 102. Plug 106 has recessed side walls 312, 314, and 316 which are generally imitate the side walls of the passage, forming two bevelled grooves or troughs (one in each side of the plug). The recessed side walls 306–310) act in opposition to the complementary recessed walls in the plug (312–316), both pairs of troughs in opposition defining two channels 302 and 304 for receiving the cable. When the plug is inserted into the body the concave troughs of the body oppose the concave grooves of the plug in such a way that they form at least one (preferably two) through channels 302 and 304. The through channels thus defined have a polygonal (preferably generally hexagonal) cross section. Thus, the channels are generally hexagonal channels in the sense that their cross section is hexagonal at any cross plane. It is not necessary that the channel be precisely hexagonal or that the angles be exactly 60 degrees; nor is it necessary that the sides be equal. The hexagonal symmetry is only approximate, being in general broken by a gap 510 between plug and body troughs.

In geometrical terms, the recessed troughs or grooves in the plug and body in opposition define at least one channel which is prismoidal. Specifically, in one embodiment the channel approximates a frustrum of a polygonal pyramid with the wider portion disposed forward (as previously defined). More specifically, the channel preferably approximates a frustrum of a hexagonal pyramid. For definitions of these geometric terms, see the *Penguin Dictionary of Mathematics*, John Daintith and R. D. Nelson, Editors (Penguin, 1989).

Preferably, a guide rail 108 projects from the plug to assist alignment with the guide groove 110 in the body 102. As can be seen from FIGS. 6 and 7, the concave faces defining the channels are not precisely parallel with the channel axis. In fact, the channels are flared from a wider front channel dimension to a narrower rear dimension, as discussed above.

Figure 9:
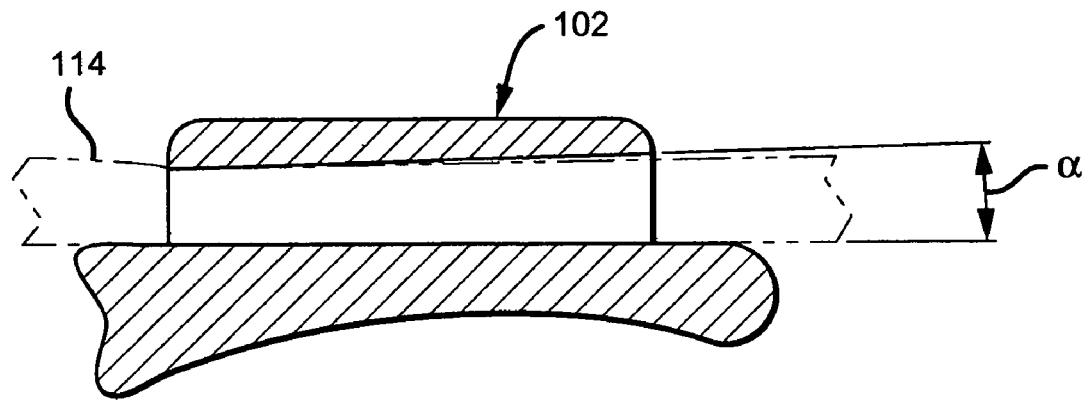
FIG. 9 is a sectional view taken along section line 9 in FIG. 2.

FIG. 9 also displays the taper of the cable channels toward a wider forward aperture, from a narrower rearward aperture (notwithstanding that the plug and the passage as a whole taper toward a narrower forward aperture).

The inventors have discovered that the unusual taper of the polygonal channels (from wider front to narrower back) in connection with a wedge-like plug tapering in the opposite sense, permits secure gripping of sheathed polymer cables at load tensions in the range up to 400 lbs for a 1.5 mm diameter polymer cable, without slippage, cutting of the cable, or abrasion of the jacket. Furthermore, the tension of the cable maintains the secure grip of the cable lock by tending to draw the wedge-like plug into the tapered channel. The cable lock is thus self-locking and retains the plug unless it is very forcibly extracted. In a preferred embodiment (with two cable strands) the plug tends to self-center in the body. The gripping power of the reverse-tapered channel is found to be superior to a channels tapered in the forward, wedging direction, without cutting the cable at high loads. The inventors believe that the unusual reverse-tapered channels act to better distribute the frictional load across the gripped section of cable, in the presence of cable deformation under tension.

The degree of flare of the channels is found to significantly affect the effectiveness of the cord lock according to the invention. Preferably, given a channel which describes a frustrum of a polyhedral pyramid, the flare should be (in a forward direction) less than 2 degrees but more than zero (0 degrees). More preferably, the convergence should 1 degree or less. Most preferably, the convergence should be 0.5 degrees or less (but more than zero). This flare is measured as the angle $\alpha$ between opposite faces of the polyhedral pyramid which would be defined by extending the channel walls backward to an imaginary vertex. The flare could also be measured by percent increase in cross sectional area, divided by length of the channel. In those terms, the preferred increase in cross sectional area is up to a twenty per cent increase from the back to the front aperture, over a linear length (in a particular embodiment) of approximately 0.385 inches. In one embodiment, for example, the cross sectional area of each hexagonal channel increases from 0.0021 to 0.0025 square inches over approximately 0.385 inches linear run.

The preferred cross sectional geometry is presently believed to be hexagonal; but other shapes could also be used, including but not limited to other polyhedral cross sections or curved cross sections. Thus, in the preferred embodiment the channels approximate a frustrum of a hexagonal pyramid wherein the angle between opposite faces converges with an angle of less than 2 degrees.

In a preferred embodiment, the plug 106 has a height dimensions that are slightly less than the height dimension of the passage 104 into which the plug is inserted. ("Height is shown vertically in FIGS. 3, 4, 6, 7 and 8). This provides a slight clearance between the plug 106 and the walls of passage 104. The clearance is visible in FIG. 8 as a gap between plug and the internal walls of the passage 104 in body 102. Most preferably, the gap or clearance completely envelops the plug and all of its features such that the plug can "float" in the passage without contact between the plug and the interior walls of passage 104. The plug is centered and caused to float thusly by the compressed cable 114 when it is retained in the channels 302 and 304. The expansive radial pressures of the compressed cable push in opposition, tending to center the plug.

The small clearance between plug and passage is desirable because it reduces or eliminates wear, which might otherwise occur from friction of plug surfaces against the passage walls. Such wear can produce very tiny particles of debris, which are undesirable in surgical implant locations.

In order to encourage the plug to float without wear, a symmetrical and generally balanced channel shape is advantageous. The center of compression in each arm of the cable should be disposed symmetrically, and preferably centered in the channel. Substantial symmetry of the channels, such as that of the regular polyhedral channel in the figures, encourages the plug to float to a suspended, stable centered position. Such a centered position will in turn reduce or eliminate surface wear within the device. Bilateral symmetry of the body and plug are also desirable, for the same reasons.

In one particular embodiment, the vertical dimensions of the interior passage exceed the vertical dimensions of the plug by 0.005 inches (at the deepest part of the groove 202 and near the rear aperture) and approximately 0.004 inches elsewhere (for the substantially plane top and bottom of the plug). This clearance will be shared between the top gap and the bottom gap, as the pressure of the compressed cable causes the plug to float to an equilibrium position. The quantitative measurement of the clearance is approximate, and given as an example. Machining tolerances or particular design considerations may cause the clearance to vary considerably from these exemplary measurements.

The body and plug are suitably made from a high strength, rigid material such as Titanium or an alloy thereof. Other alloys or materials, including polymers, may be used in some embodiments. However, Titanium or stainless steel alloys are currently thought to be preferably in medical implant applications. The pieces may be manufactured by EDM (electrical discharge machining), by metal injection molding, or other methods, preferably taking care to properly texture the channels as discussed above.

In a typical embodiment, the channels 302 and 304 should not be machined smooth, but rather should have some degree of texture or grain. For example, the channels can be machined by Electrical discharge machining (EDM) which will leave sufficient texture to engage polymer fiber securely. Alternatively, the channel can be abraded by glass bead finish process. On the other hand, the channel should be free from sharp teeth or aggressive barbs (such as those characterizing some prior cord locks, see U.S. Pat. No. 4,156,574). Although the texture has been found significant for holding smooth jacketed polymer cables, in some applications the texture may not be absolutely required.

Another aspect of the invention is a system of cable and cable lock, suitable for establishing and sustaining high tensile connection and adaptable for surgical use. The system comprises essentially the cable lock described above in concert with a strong and elastic cable. In one embodiment, the cable is an engineered polymer cable comprising at least one core filament (suitably nylon), coaxially surrounded by a woven jacket. The braided jacket preferably comprises woven fibers of an ultra-high molecular weight polymer material such as that sold by Honeywell Corp. (Allantown, Pa.) under the trade name "spectra"™.

Figure 10:
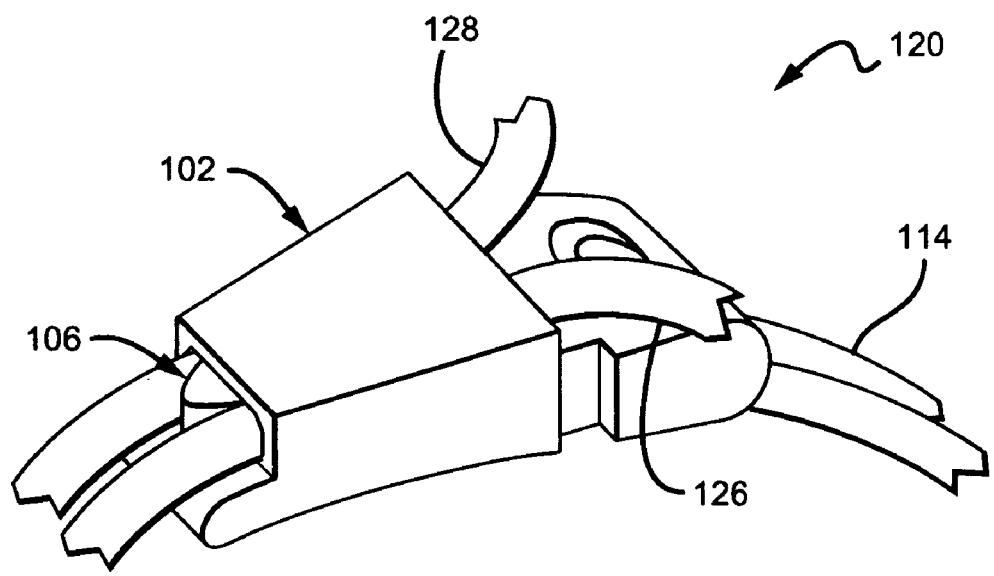
FIG. 10 is a perspective view of a cable and clamp in a doubled cable configuration, suitably for fixation of surgical cerclage at very high tensions.

In one embodiment, the cable clamp as described above is used in concert with a polymer cable capable of achieving elongation which increases the polymer cable by a percentage between 60 and 140 per cent of its original length, at a working tension up to approximately 800 Newtons. The working force is commonly doubled by doubling the cable as shown in FIGS. 1 and 10. A suitable cable can be engineered from nylon core and Spectra™ jacket. Preferably the jacket should be coated with a coating to enhance grip and insulate the cable from biological hydrolysis.

In concert with the cable described above, a cable clamp in accordance with the invention is found to be effective at tensions up to 350 lbs per strand. Note that the tensions have been given in lbs for each cable end. In a typical embodiment, as shown in FIGS. 1 and 10, the cable has both ends engaged (one on each side of the wedged plug) and thus the clamp can support double the tension of a single cable. Even more specifically, in one embodiment the cable ends 126 and 128 comprise two ends of a looped cable, doubled at the end. The doubled end can be retained by the body by threading the ends through the holes 122 and 124 and roughly centering the body near the middle of the cable, as shown in FIG. 1. The body thus retains in a through bore the middle of a doubled cable. The doubled ends can be passed around a system, tensioned, and clamped by the tapered plug and body of the clamp as shown (and as previously described). Such an arrangement is a convenient method of providing cerclage for surgical procedures, for example in compressing a fractured femur (with or without a plate to align the bones).

The invention also includes a method of retaining a high tension cable, suitable for use to attach cables during surgery. In accordance with the method, a cable is included in a cable clamp as described above: having at least one tapered channel between a body and a slidable plug, with a free end emerging from a rear end of the body, and a working end emerging from a forward end of said body. The slidable plug and body are tapered and adapted to constrict around said cable as the slidable plug slides toward a forward end of the body. As discussed above in connection with the apparatus, the cable is received in a tapered channel which flares outward in the forward direction. Tension is then applied to the cable in a forward direction, while applying reactive force to the body in the opposite direction. The plug responds the cable tension by sliding forward, wedging securely in the tapered body and engaging the cable in a channel. The channel has a forward flare, opening in the direction toward the source of tension. Thus, the wedge and body constrict in response to sliding of the plug in the forward direction; nevertheless, the cable channel flares outward in the forward direction.

While several illustrative embodiments of the invention have been shown and described, numerous variations and alternate embodiments will occur to those skilled in the art. For example, although the invention is shown and described with two channels, more generally the invention may include any configuration with at least one such channel. Two channels are preferred; one reason is that two such channels in opposition tends to promote stability and self centering action. Thus, a preferred embodiment has two such channels in opposition. Variations and alternate embodiments are contemplated, and can be made without departing from the spirit and scope of the invention as defined in the appended claims.

I Claim:

1. A cable retaining device, suitable for retaining flexible cables at high load tensions, comprising:
    a body including a void having a width that tapers from a wider rearward end to a narrower forward end; and
    a tapered plug, capable of slidable insertion at least partially into said void;
    wherein said void and said plug define at least one channel between them, said channel capable of receiving a cable; and
    wherein said channel is flared from a narrower rearward orifice disposed toward said wider rearward end of said void in said body, to a wider forward orifice disposed toward said narrower forward end of said void.

2. The cable retaining device of claim 1, wherein said channel has a substantially polygonal cross section.

3. The cable retaining device of claim 2, wherein said polygonal cross section is substantially hexagonal.

4. The cable retaining device of claim 3, wherein said channel tapers with an angle of less than 1 degrees.

5. The cable retaining device of claim 4, wherein said angle is greater than zero but less than or equal to 0.5 degrees.

6. The cable retaining device of claim 3, wherein said channel has a cross section which flares linearly, increasing in cross section from said rearward end to said forward end.

7. The cable retaining device of claim 3, wherein said plug has an outer dimension less than a complementary interior dimension of said void, defining a clearance between said plug and an interior surface of said void, when said plug is inserted into said void.

8. A system of cable and cable lock, suitable for establishing and sustaining high tensile connection and adaptable for surgical use, comprising:
    a cable lock comprising a body and a wedge, insertable into said body;
    said wedge tapering from a wider rearward end to relatively narrower forward end, said taper defining a forward direction:
    said body and said wedge each having at least one opposable, complementary groove on at least one side, a wedge groove and a body groove in opposition defining at least one cable channel between said wedge and said body wherein said channel is flared from a narrower rearward orifice disposed toward a wider rearward end of a void in said body, to a wider forward orifice disposed toward a narrower forward end of said void;
    a polymer cable, passed through said cable channel, said cable having a free end and a loaded end, said cable comprising:
        a polymer core, and
        a braided polymer jacket;
    wherein at least a portion of said cable channel is flared outward in said forward direction, thereby opening in the direction toward the loaded and of said cable.

9. The cable system of claim 8, wherein said grooves each have three faces generally describing a bisected hexagon, said body groove and said wedge groove in opposition describing a channel generally hexagonal in cross section.

10. The cable system of claim 9, wherein said channel flares at an angle in the range less than one degree.

11. The cable system of claim 10, wherein said angle is greater than zero but less than or equal to 0.5 degrees.

12. The cable system of claim 9, wherein said cable jacket comprises an ultra-high molecular weight polymer material.

13. The cable system of claim 8, wherein said cable has tensile strength of at least 100 pounds and is capable of elongation in the range of 60 to 140 per cent over its original length.

14. A method of retaining a high tension cable, comprising the steps of:

including said cable in at least one tapered channel between a body and a slidable plug, with a free cable end emerging from a rear end of said body, and a forward cable end emerging from a forward end of said body;

said slidable plug and body tapered and adapted to constrict around said cable as said slidable plug slides toward said forward end of said body; and applying tension to the forward cable end, to set said plug and clamp said cable;

wherein said channel is flared from a narrower rearward orifice disposed toward a wider rearward end of a void in said body, to a wider forward orifice disposed toward a narrower forward end of said void.

15. The method of claim 14, wherein said channel is flared outwardly at an angle in the range greater than 0 but less than 1.0 degrees.

16. The method of claim 15, wherein said channel is generally hexagonal in cross section.

17. The method of claim 14, wherein said step of applying tension comprises:

applying tension in the range from 100 to 350 lbs.

18. The method of claim 14, wherein said plug and said body define two said channels, with one on each side of said plug, arranged to receive two cables or two ends of the same cable in tension.

\* \* \* \* \*